(12) United States Patent
Tran et al.

(10) Patent No.: US 11,904,047 B1
(45) Date of Patent: Feb. 20, 2024

(54) FORMULATION AND DELIVERY SYSTEMS FOR HERBAL COMPOSITIONS FOR THE TREATMENT OF CANKER SORES (RECURRENT APHTHOUS STOMATITIS) AND RELATED CONDITIONS

(71) Applicants: Sandie Tran, San Diego, CA (US); Sang Nguyen, Seal Beach, CA (US)

(72) Inventors: Sandie Tran, San Diego, CA (US); Sang Nguyen, Seal Beach, CA (US)

( * ) Notice: Subject to any disclaimer, the term of this patent is extended or adjusted under 35 U.S.C. 154(b) by 9 days.

(21) Appl. No.: 17/648,845

(22) Filed: Jan. 25, 2022

Related U.S. Application Data

(63) Continuation of application No. 16/948,980, filed on Oct. 8, 2020, now abandoned.

(51) Int. Cl.
| | |
|---|---|
| *A61K 9/00* | (2006.01) |
| *A61K 36/9066* | (2006.01) |
| *A61K 9/68* | (2006.01) |
| *A61K 31/165* | (2006.01) |
| *A61K 36/185* | (2006.01) |
| *A61K 36/61* | (2006.01) |
| *A61K 36/54* | (2006.01) |
| *A61K 36/906* | (2006.01) |
| *A23L 33/105* | (2016.01) |
| *A61K 36/81* | (2006.01) |
| *A61K 45/06* | (2006.01) |
| *A61K 36/9068* | (2006.01) |

(52) U.S. Cl.
CPC .......... *A61K 9/0056* (2013.01); *A23L 33/105* (2016.08); *A61K 9/0058* (2013.01); *A61K 31/165* (2013.01); *A61K 36/185* (2013.01); *A61K 36/54* (2013.01); *A61K 36/61* (2013.01); *A61K 36/81* (2013.01); *A61K 36/906* (2013.01); *A61K 36/9066* (2013.01); *A61K 36/9068* (2013.01); *A61K 45/06* (2013.01)

(58) Field of Classification Search
CPC .. A61K 9/0056; A61K 9/0058; A61K 31/165; A61K 36/185; A61K 36/54; A61K 36/61; A61K 36/81; A61K 36/906; A61K 36/9066; A61K 36/9068; A61K 45/06; A23L 33/105
See application file for complete search history.

(56) References Cited

U.S. PATENT DOCUMENTS

| | | |
|---|---|---|
| 5,376,374 A | 12/1994 | Zelaya |
| 5,762,963 A | 6/1998 | Byas-Smith |
| 5,788,982 A | 8/1998 | Nadoolman et al. |
| 6,592,896 B2 | 7/2003 | Rosenbloom |
| 6,827,945 B2 | 12/2004 | Rosenbloom |
| 2006/0264497 A1 | 11/2006 | Zeligs |
| 2010/0303935 A1 | 12/2010 | Squires |
| 2016/0074298 A1 | 3/2016 | Birbara et al. |
| 2018/0303888 A1 | 10/2018 | Cho et al. |

FOREIGN PATENT DOCUMENTS

| | | | |
|---|---|---|---|
| CN | 102048880 A | 5/2011 | |
| TW | M538398 U | * 3/2017 | ............... A61K 9/16 |
| WO | 2009097512 A1 | 8/2009 | |
| WO | WO-2018129315 A1 | * 7/2018 | |

* cited by examiner

*Primary Examiner* — Aaron J Kosar
(74) *Attorney, Agent, or Firm* — INNOVATION CAPITAL LAW GROUP, LLP; Vic Lin

(57) ABSTRACT

An herbal composition includes a plurality of herbal components designed to work harmoniously together to alleviate pain and reduce inflammation of the oral mucosa. Such pain and inflammation may be associated with, for example, recurrent aphthous stomatitis. The formulation can include ginger, cayenne, cloves, cinnamon, turmeric, and annatto. The herbal composition may be formulated as a candy or gum, for example, to provide effective delivery to the oral mucosa.

27 Claims, No Drawings

FORMULATION AND DELIVERY SYSTEMS FOR HERBAL COMPOSITIONS FOR THE TREATMENT OF CANKER SORES (RECURRENT APHTHOUS STOMATITIS) AND RELATED CONDITIONS

CROSS-REFERENCE TO RELATED APPLICATIONS

This application is a continuation of U.S. Non-Provisional patent application Ser. No. 16/948,980, filed Oct. 8, 2020, the disclosure of which is incorporated by reference herein.

BACKGROUND OF THE INVENTION

1. Field of the Invention

Embodiments of the invention relate generally to pharmaceutical compositions and methods for using the same. More particularly, embodiments of the invention relate to a formulation and delivery system for herbal compositions for the treatment of recurrent aphthous stomatitis and related conditions.

2. Description of Prior Art and Related Information

The following background information may present examples of specific aspects of the prior art (e.g., without limitation, approaches, facts, or common wisdom) that, while expected to be helpful to further educate the reader as to additional aspects of the prior art, is not to be construed as limiting the present invention, or any embodiments thereof, to anything stated or implied therein or inferred thereupon.

Recurrent aphthous stomatitis (RAS) is a common disease of the oral mucosa characterized by the recurrent development of one to several discrete, painful ulcers that typically heal within two weeks. RAS is classified as either simple aphthosis or complex aphthosis. Simple aphthosis is the more common form of the disease, occurs worldwide, and is reported in every populated continent with a prevalence rate of 25%. Patients experience several self-limiting episodes per year, and involvement is limited to the oral mucosa. It is well recognized that the symptoms caused by recurrent or chronic oral mucosal lesions, such as pain during speaking, eating, and swallowing, can deeply affect the oral health-related quality of life of patients.

The diagnosis of RAS is usually made on clinical grounds, based upon a typical history and physical exam. The common characteristic of RAS presents as recurrent solitary or multiple, shallow, round or ovoid, and self-limiting ulcers with an erythematous, raised margin, and a yellow-grayish floor. Simple RAS, by far the most common type, appear as small ulcers (5-10 mm) and heal spontaneously in 7-14 days. Most patients are otherwise healthy. Pain is the major symptom that starts in the first 24 hours as a tingling or mild irritant sensation, and then ascends and peaks during the first 3-4 days. Although the disease is self-limiting, the pain can lead to debilitating oral functionality and impaired food and fluid intake, resulting in subsequent dehydration and other complications.

Etiology of RAS is still unclear and thought to be multifactorial with precipitating factors such as hematologic deficiency, food hypersensitivity, familial tendency, medications, hormone imbalance, immunologic abnormalities, and imbalance of oral microbiome. Additionally, some studies have suggested that stress may serve as a trigger or a modifying factor for RAS.

Current approaches to the management of RAS is palliative with a primary goal of pain alleviation, reduction of ulcer duration, prevention of superinfection, and restoration of oral functions.

Many topical agents have been used with variable success. Given the lack of clarity regarding the etiology of RAS, there is no definitive or uniformly effective therapy for RAS. Although many attempts, including topical medications in the form of gels, creams, pastes, ointments, sprays, and rinses have been developed with varying success, such forms are invariably diluted and eliminated from the oral mucosa due to the flushing effect of saliva. Hence, the therapeutic efficiency of the agent decreases upon contact with the oral cavity. At present, there are numerous herbal formulations claiming to treat RAS, although none that are in widespread use.

Furthermore, current treatments are not ideal due to their unpleasant taste and texture. Some treatment options can sting on contact with the ulcer, while others use a bio-adhesive cover that is not user friendly.

U.S. Pat. No. 5,788,982A uses capsaicin in a candy, to reduce pain for oral mucositis. However, in a corresponding article, the authors noted that application of capsaicin itself caused burning pain and limited its usefulness. According to the authors, the spontaneous burning pain and hyperalgesia are believed to be due to intense activation and temporary sensitization of the peripheral nociceptors at the site of capsaicin application. This activation and sensitization occur prior to the desensitization phase. Hence, the activation phase may be a barrier to the use of capsaicin due to the burning sensation. The authors speculated that it is possible that some of the pain produced by mucositis is mediated by neurons that are not desensitized by capsaicin. The authors also suggested that further research and improvements are needed to help decrease undesirable effects of capsaicin.

In view of the foregoing, there is a need for improved compositions and methods for the treatment and management of RAS.

SUMMARY OF THE INVENTION

Aspects of the present invention are designed to reduce pain and promote healing as a first-line therapy for recurrent aphthous stomatitis (RAS). Aspects of the present invention can improve upon existing art in the field by providing a safe and effective delivery system using an herbal formulation in a candy or gum to reduce pain and inflammation for RAS and related conditions.

Aspects of the present invention are based on the understanding that current treatment options have limited contact time of active ingredients to the mucosal lining of the affected area. Various treatments and products, in the form of sprays, gels, or viscous solutions, are currently marketed, but the effect is limited, because contact time with the oral mucosa is minimal. The formulation in the present invention helps to enhance the contact time of the active ingredients to the ulcer area.

In addition, current treatments are not ideal due to their unpleasant taste and texture. Some treatment options can sting on contact with the ulcer, while others use a bio-adhesive cover that is not user friendly. The inventors discovered that the formulation of herbals according to aspects of the present invention works harmoniously to improve tolerability and palatability, and, consequently, better acceptance by patients.

Embodiments of the present invention provide a formulation comprising active ingredients including from about 2 to about 70 weight percent annatto; from about 0.05 to about 40 weight percent cayenne; from about 5 to about 30 weight percent cinnamon; from about 0.05 to about 50 weight percent cloves; from about 0.1 to about 60 weight percent ginger; and from about 1 to about 70 weight percent turmeric.

In some embodiments the annatto is present from about 20 to about 36 weight percent; the cayenne is present from about 5.6 to about 10.4 weight percent; the cinnamon is present from about 8.4 to about 16 weight percent; the cloves are present from about 11 to about 21 weight percent; the ginger is present from about 10 to about 18 weight percent; and the turmeric is present from about 15 to about 29 weight percent.

In some embodiments, the annatto is present at 28 weight percent; the cayenne is present at 8 weight percent; the cinnamon is present at 12 weight percent; the cloves are present at 16 weight percent; the ginger is present at 14 weight percent; and the turmeric is present at 22 weight percent.

In some embodiments, the formulation further comprises inactive ingredients operable to form a gum. In some embodiments, the inactive ingredients of the gum include confectioner's sugar, corn syrup and gum pellets. In some embodiments, the active ingredients of the gum are present at about 5 to about 20 weight percent of the gum. In some embodiments, the active ingredients of the gum are present at about 10 to about 15 weight percent of the gum. In some embodiments, the active ingredients of the gum are present at about 12 weight percent of the gum.

In some embodiments, the formulation further comprising inactive ingredients operable to form a hard candy. In some embodiments, the hard candy is a lollipop. In some embodiments, the inactive ingredients of the hard candy include granulated sugar, corn syrup and water. In some embodiments, the active ingredients of the hard candy are present at about 3 to about 20 weight percent of the hard candy. In some embodiments, the active ingredients of the hard candy are present at about 6 to about 10 weight percent of the hard candy. In some embodiments, the active ingredients of the hard candy are present at about 7.8 weight percent of the hard candy.

In some embodiments, the formulations described above may be useful for the treatment and/or prevention of recurrent aphthous stomatitis, pain of the oral mucosa, inflammation of the oral mucosa, and the like.

Embodiments of the present invention further provide a method for treating recurrent aphthous stomatitis comprising delivering, to a patient in need thereof, a pharmaceutically effective amount of a composition comprising active ingredients including from about 2 to about 70 weight percent annatto; from about 0.05 to about 40 weight percent cayenne; from about 5 to about 30 weight percent cinnamon; from about 0.05 to about 50 weight percent cloves; from about 0.1 to about 60 weight percent ginger; and from about 1 to about 70 weight percent turmeric.

In some embodiments, the active ingredients are present at about 3 to about 20 weight percent of the composition.

Embodiments of the present invention also provide a method for treating oral mucosa pain and/or inflammation comprising delivering, to a patient in need thereof, a pharmaceutically effective amount of a composition comprising active ingredients including from about 2 to about 70 weight percent annatto; from about 0.05 to about 40 weight percent cayenne; from about 5 to about 30 weight percent cinnamon; from about 0.05 to about 50 weight percent cloves; from about 0.1 to about 60 weight percent ginger; and from about 1 to about 70 weight percent turmeric.

In some embodiments, the composition is formulated as one of a gum or a lollipop.

These and other features, aspects and advantages of the present invention will become better understood with reference to the following drawings, description and claims.

DETAILED DESCRIPTION OF THE PREFERRED EMBODIMENTS AND BEST MODE OF INVENTION

The terminology used herein is for the purpose of describing particular embodiments only and is not intended to be limiting of the invention. As used herein, the term "and/or" includes any and all combinations of one or more of the associated listed items. As used herein, the singular forms "a," "an," and "the" are intended to include the plural forms as well as the singular forms, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof.

Unless otherwise defined, all terms (including technical and scientific terms) used herein have the same meaning as commonly understood by one having ordinary skill in the art to which this invention belongs. It will be further understood that terms, such as those defined in commonly used dictionaries, should be interpreted as having a meaning that is consistent with their meaning in the context of the relevant art and the present disclosure and will not be interpreted in an idealized or overly formal sense unless expressly so defined herein.

In describing the invention, it will be understood that a number of techniques and steps are disclosed. Each of these has individual benefit and each can also be used in conjunction with one or more, or in some cases all, of the other disclosed techniques. Accordingly, for the sake of clarity, this description will refrain from repeating every possible combination of the individual steps in an unnecessary fashion. Nevertheless, the specification and claims should be read with the understanding that such combinations are entirely within the scope of the invention and the claims.

In the following description, for purposes of explanation, numerous specific details are set forth in order to provide a thorough understanding of the present invention. It will be evident, however, to one skilled in the art that the present invention may be practiced without these specific details.

The present disclosure is to be considered as an exemplification of the invention and is not intended to limit the invention to the specific embodiments illustrated by the FIGURES or description below.

As is well known to those skilled in the art, many careful considerations and compromises typically must be made when designing for the optimal configuration of a commercial implementation of any composition, and in particular, the embodiments of the present invention. A commercial implementation in accordance with the spirit and teachings of the present invention may be configured according to the needs of the particular application, whereby any aspect(s), feature(s), function(s), result(s), component(s), approach(es), or step(s) of the teachings related to any described embodiment of the present invention may be suitably omitted, included, adapted, mixed and matched, or improved and/or optimized by those skilled in the art, using their average skills and known techniques, to achieve the desired implementation that addresses the needs of the particular application.

Broadly, embodiments of the present invention provide an herbal composition including a plurality of herbal components designed to work harmoniously together to alleviate pain and reduce inflammation of the oral mucosa. Such pain and inflammation may be associated with recurrent aphthous stomatitis. The formulation includes ginger, cayenne, cloves, cinnamon, turmeric, and annatto. The herbal composition may be formulated as a candy or gum, for example, to provide effective delivery to the oral mucosa. The table below outlines exemplary ingredients in an herbal composition according to embodiments of the present invention.

| Active herbal ingredients | |
|---|---|
| Ingredient | Benefit |
| Bixin | Antimicrobial; Analgesic; and Antioxidant |
| Capsaicin | Antimicrobial; Analgesic; and Works synergistically with gingerol for pain |
| Cinnamaldehyde | Antimicrobial (Works synergistically with eugenol); and Antioxidant |
| Curcumin | Inhibits phosphorylase kinase activity; Downregulates transcription factors, cytokines, adhesion molecules, cyclin kinase, and protein kinase; Induces apoptosis in damaged cells, increasing rapid replacement of injured cells; Blocks activation of NF-kB transcription activator. NF-kB is responsible for activating 200 genes related to proliferation of inflammatory cells; Better absorption through topical curcumin; and Anti-inflammatory |
| Eugenol | Anti-inflammatory, neuroprotective, antipyretic, antioxidant, antifungal and analgesic properties; Produces trans receptor potential vanilloid-1 (TRPV-1), which desensitizes nerve endings near the surface of the skin, pain reliever, numbing effect, and promotes circulation; and Antimicrobial synergy with cinnamon |
| Gingerol | Antioxidant; Anti-inflammatory, reduce swelling, reduce pain; Analgesic; and Works synergistically with capsaicin and considered as full agonists of VR1 receptor |

Ginger (*Zingiber officinale* Roscoe) is a well-known and widely used spice and condiment, especially in Asia. Gingerol, also known as 6G [6]-gingerol or (6)-gingerol, belongs to the class of organic compounds known as gingerols. Gingerols are compounds containing a gingerol moiety, which is structurally characterized by a 4-hydroxy-3-methoxyphenyl group substituted at the C6 carbon atom by a 5-hydroxy-alkane-3-one. The rhizome of ginger contains several interesting bioactive constituents and possesses health-promoting properties. The pungency of fresh ginger is primarily due to the gingerols which are a homologous series of phenolic compounds, whereas the pungency of dried ginger is mainly due to the presence of shogaols, mainly (6)-shogaol, which are dehydrated forms of gingerols. Some potential benefits of ginger include analgesic, anti-inflammatory, antioxidant, and cardioprotective properties.

The structure of gingerol is very similar to capsaicin, in which the active component interacts with the vanilloid (VR1) receptor on cell membranes that are involved in controlling influx of calcium and sodium and facilitating nociceptive signals. Gingerol can work with capsaicin and can be considered as a full agonist of the VR1 receptor. Thus, embodiments of the present invention can use gingerol to provide additive and/or synergistic pain relief by also exploiting the activation of the VR1 receptor, in a mechanism similar to that of capsaicin.

Peppers, such as cayenne, have been widely used to enhance cuisine for thousands of years. The predominant active ingredient in chili peppers (plants from the Solanaceae family) is the parent compound capsaicin, which gives chili peppers their pungency. The chemical name of capsaicin is (E)-N-[(4-hydroxy-3-methyoxyphenyl)methyl]-8-methyl-6-nonenamide and has the structure shown in formula (I), below. As a class, they are known as capsaicinoids. Capsaicinoids include dihydrocapsaicin, norhydrocapsaicin, homocapsaicin, homodihydrocapsaicin I, norhydrocapsaicin, homodihydrocapsaicin, nordihydrocapsaicin, civamide, nonivamide, NE-19550 (also called olvanil), NE-21610, NE-28345 (also called N-oleylhomovanillamide, their analogs, and derivatives.

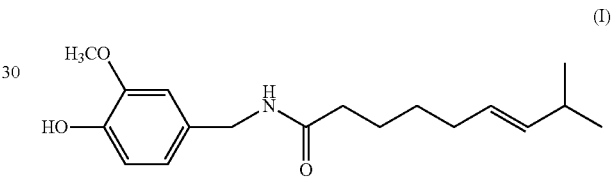

(I)

Studies have shown analgesic effects of capsaicin, and there are many formulations of capsaicin available over the counter in various concentrations. However, many have dose limiting side effects. Capsaicin triggers C-fiber and A-delta fibers that are believed to signal pain. It appears that capsaicin triggers C-fiber membrane depolarization by opening cation channels permeable to calcium and sodium. Capsaicin mediated effects include: 1) activation of nociceptors in peripheral tissues; 2) eventual desensitization of peripheral nociceptors to one or more stimulus modalities; 3) cellular degeneration of sensitive A-delta and C-fiber afferents; 4) activation of neuronal proteases; 5) blockage of axonal transport; and 6) the decrease of the absolute number of nociceptive fibers without affecting the number of non-nociceptive fibers.

Cloves are the flower buds of the clove tree, an evergreen also known as *Syzygium aromaticum*. They are a popular spice that people use in soups, stews, meats, sauces, and rice dishes. In addition to their sweet, aromatic flavor, cloves are known for their potent medicinal properties. People have used cloves in cooking and traditional medicine for many years, but it is only recently that scientists have begun studying their potential health benefits. Cloves include 90-95% eugenol, and some other minor constituents. A major component of clove taste is imparted by the chemical eugenol. Eugenol is the component which is most responsible for clove aroma and comprises 72-90% of the essential oil extracted from cloves. Other important essential oil constituents of clove oil are acetyl eugenol, beta-caryophyllene and vanillin, crategolic acid, tannins such as bicornin, methyl salicylate (painkiller), gallotannic acid, the flavonoidseugenin, rhamnetin, kaempferol, and eugenitin, triterpenoids such as oleanolic acid, campesterol and stigmasterol, and several sesquiterpenes.

The following are properties in cloves: 1) ortho-eugenol has antinociceptive activity mediated by the adrenergic system; 2) ortho-eugenol reduces levels of IL-13 and TNF-αt proinflammatory cytokines, and 3) ortho-eugenol exhibits anti-inflammatory effects by virtue of NF-kB-p and p-p38 suppression. Clove oil has been studied as a natural method for maintaining oral health due to its effect on plaque, gingivitis, and bacteria in the mouth. One of the most notable potential pain-relieving benefits of cloves is their ability to help with toothaches due to the eugenol they contain, which acts as a natural antiseptic. In fact, it was found they work better at relieving pain, inflammation, wound healing, and infection than another common option (chlorhexidine). In addition to the anti-inflammatory and anti-bacterial actions of cloves, it is believed that their sweet and aromatic flavor plays a role in balancing the pungency of the capsaicin and ginger in the formulations according to aspects of the present invention.

Cinnamon (*Cinnamomum zeylanicum*, and Cinnamon cassia), the eternal tree of tropical medicine, belongs to the Lauraceae family. There are many types of cinnamon. Ceylon cinnamon (*Cinnamomum verum*), grown primarily in Sri Lanka, is known as "true" cinnamon. Cassia cinnamon (*Cinnamomum aromaticum*), grown in southeastern Asia, is the most common type sold in North America. Cinnamon is one of the most important spices used daily by people all over the world. This plant not only plays a vital role as a spice, but its essential oils and other constituents also have important activities, including antimicrobial, antifungal, antioxidant, and antidiabetic, anti-inflammatory, antimycotic, and anticancer agent activities. Additionally, cinnamon and cloves can have synergistic antimicrobial effects. Cinnamon has also been traditionally used as tooth powder to treat toothaches, dental problems, oral microbiota, and bad breath. With these characteristics, cinnamon was chosen to be a part of the formulations according to aspects of the present invention. It was discovered that cinnamon makes the formulation more palatable, and may provide additional and/or synergistic analgesic, anti-inflammatory, and antimicrobial effects.

Curcumin (diferuloylmethane) is one of the ingredients found in the spice, turmeric. Turmeric has been used for centuries in many eastern countries, both as a spice and as a medicine. Major phytoconstituents of turmeric are diarylheptanoids, which occur in a mixture termed curcuminoids that generally make up approximately 1-6% of turmeric by dry weight. Curcumin is the major biologically active polyphenolic constituent in turmeric. Two other curcuminoids occur in lesser amounts, namely demethoxycurcumin (DMC) and bis-demethoxycurcumin (BDMC). Curcumin is widely known to have anti-inflammatory properties. In cell cultures, it has been shown to suppress the proliferation of a wide variety of tumor cells, downregulate transcription factors (NF-kB, AP-1), downregulate the expression of cytokines (TNF-α), cell surface adhesion molecules and cyclin D, and inhibit the activity of c-Jun N-terminal kinase, protein tyrosine kinase, and protein serine/threonine kinases. Curcumin has been reported to induce apoptosis in damaged cells. The removal of damaged cells by apoptosis allows the space for replacement by new, healthy cells. These characteristics make turmeric a choice for inclusion in aspects of the formulation of the present invention, which not only focuses on pain relief, but also seeks to speed wound healing in mouth ulcers.

Annatto is a natural food coloring and condiment that is extracted from the seeds of the achiote fruit. The achiote tree (*Bixa orellana*) is a tropical shrub or small tree that grows in Central and South America. The flowers of this tropical tree are white or bright pink, but the fruit is the most desirable part of the plant, made up of spiky brown and red pods that grow in clusters. The seeds are covered with a slightly waxy, clay-like substance that produces a bright yellow or orange stain. When those pods dry and crack open, they expose seeds of red color, from which red pigment can be extracted. It has a floral and nutty smell and is mildly peppery to taste.

In the Caribbean and Central American cultures, annatto has been used for thousands of years to treat everything from mild to potentially life-threatening diseases, making it an ancient "superfood." Annatto has a rich source of antioxidants such as cis-bixin, carotenoids, and vitamin A. Annatto, due to its powerful antioxidants, possesses antimicrobial properties and powerful antioxidants that help fight cell damage and it can kill various pathogens, and bacteria in the body. Annatto paste has been used with success to heal wounds due to the presence of antioxidants. Bixin, a red-colored carotenoid, is the pigment present in high concentration in the annatto seed aril. Bixin has a chain of 25 carbons and has the molecular formula $C_{25}H_{30}O_4$ (MW=394.51). It has a carboxylic acid and methyl ester group at the ends of the chain. Bixin occurs in nature as the 16-Z form (cis), but during the extraction process it isomerizes resulting in the 16-E form (trans), which is called isobixin.

According to embodiments of the present invention, it has been discovered that annatto's waxy and clay-like characteristic and lipid solubility acts like a bio adhesive to enhance contact time of the formulation to the oral mucosa and helps with desensitization to the cayenne. In addition, its earthy and nutty taste worked in conjunction with the cinnamon to harmonize the other ingredients in this formulation, making the treatment more acceptable and effective.

For reasons above, the herbal composition according to aspects of the present invention can help provide additive and/or synergistic pain relief, improve taste, and thus create better tolerance and acceptance for patients. To circumvent those issues encountered with current treatment options, aspects of the present invention are designed to work with saliva by administering the herbal formulation in a gum or candy, such as a lollipop. The active ingredients (the herbal composition) can be uniformly distributed and continuously delivered using saliva as part of the delivery mechanism. Based on this strategy, candy or gum could act as a vehicle since these delivery systems may be held in the mouth for a longer duration, and thus provide longer contact time of active ingredients as well as facilitate desensitization of the capsaicin. As a result, using a gum or candy comprising of herbal ingredients can reduce pain and inflammation, along with other benefits, and can result in significant symptomatic relief and improved outcomes for patients suffering from RAS and other related ulcers of the oral and pharyngeal mucus membrane.

In some embodiments, the herbal composition can include the following ingredients:
(a) from about 2 to about 70 weight percent annatto;
(b) from about 0.05 to about 40 weight percent cayenne;
(c) from about 5 to about 30 weight percent cinnamon;
(d) from about 0.05 to about 50 weight percent cloves;
(e) from about 0.1 to about 60 weight percent ginger; and
(f) from about 1 to about 70 weight percent turmeric.

Typically, the herbal composition can include the following ingredients:

(a) from about 20 to about 36 weight percent annatto;
(b) from about 5.6 to about 10.4 weight percent cayenne;
(c) from about 8.4 to about 16 weight percent cinnamon;
(d) from about 11 to about 21 weight percent cloves;
(e) from about 10 to about 18 weight percent ginger; and
(f) from about 15 to about 29 weight percent turmeric.

In some embodiments, the herbal composition can include the following ingredients:

(a) 28 weight percent annatto;
(b) 8 weight percent cayenne;
(c) 12 weight percent cinnamon;
(d) 16 weight percent cloves;
(e) 14 weight percent ginger; and
(f) 22 weight percent turmeric.

Study

The study protocol was to administer the composition via two modalities (gum and candy). Both were administered orally within 48 hours of onset of RAS. The inclusion criteria to participate in the study were as follows: 1) age >18 years, 2) have a history of RAS occurring at least twice a year, and 3) presenting at least one active ulcer less than 48 hours duration from onset measuring no more than 10 mm in diameter.

Patients with 1) systemic diseases, 2) taking systemic antibiotics, non-steroidal anti-inflammatory drugs, immunomodulatory agents, or local mediation within 1 month prior to the study, and 3) with any known allergies to the substances in the composition, were excluded from the study. Twenty patients were observed (10 for gum; 10 for lollipop). A Visual Analog Scale (VAS) was administered pre- and post-treatment using a 10 cm line labeled on the high end as "worse possible soreness" and the low end as "no soreness."

Gum Example

Patients were treated with a composition formed with an herbal composition having ingredients as shown in the table below. The table also provides suitable ranges for each ingredient as may be used in an herbal composition in a gum formulation. The w/w percentages listed in the below table are based on the weight of the gum, as described below.

| Composition (% of weight-weight) of individual herbal ingredients for gum | | |
|---|---|---|
| Ingredient | % (w/w) | Ranges % (w/w) |
| Annatto | 3.4% | 0.05-30% |
| Cayenne | 1% | 0.01-20% |
| Cinnamon | 1.4% | 0.25-40% |
| Cloves | 1.9% | 0.01-30% |
| Ginger | 1.7% | 0.01-40% |
| Turmeric | 2.6% | 0.25-60% |

The herbal composition as described above can be formulated into a gum composition as shown in the table below. In should be understood that other gum formulations, as known to one skilled in the art, may be used in the present invention.

| Ingredients for gum (242 g total, 5 g each gum) | |
|---|---|
| Ingredient | Amount |
| Confectioner's Sugar | 5.3 g |
| Corn Syrup | 15 g |
| Gum Pellets | 193 g |
| Herbal Composition | 28.8 g |

The composition was delivered via a chewing gum weighing 5 g each. Patients were assessed every 15 minutes over a 2-3 hour time period. Prior to treatment, the following steps were undertaken: 1) visual diagnosis focusing on the minor ulcer with a well-demarcated ulcer on the non-keratinized oral mucosa, and 2) patients were asked to complete a pre-treatment VAS.

Patients were then directed to chew on the gum for a minimum of 15 minutes during which saliva production and release of the composition provided uniform distribution on the whole surface of the oral mucosa. Patients were not refrained from eating or drinking immediately after chewing. The patient was then instructed to use the gum as needed for the next five consecutive days.

After the first administration, a post-treatment VAS was provided to assess the scale of the pain. The assessment indicated that, in all cases, patients' perceived pain was reduced by 50-83%. The patients indicated that the composition tasted good, was well tolerated, and provided normal oral functionality. All patients reported comparable pain relief on subsequent uses of the gum until resolution of canker sore. The table below provides the pre- and post-treatment VAS scores.

| Pre- and Post- Treatment VAS Scores (10 cm) using gum | | | |
|---|---|---|---|
| Patient | Pain before gum | Pain after gum | Pain Relief | Duration of relief (hrs) |
| 1 | 6 | 2 | Yes | 2 |
| 2 | 7 | 3 | Yes | 1.5 |
| 3 | 6 | 3 | Yes | 1.5 |
| 4 | 6 | 1 | Yes | 2 |
| 5 | 6 | 2 | Yes | 1 |
| 6 | 5 | 2 | Yes | 2 |
| 7 | 5 | 2 | Yes | 1 |
| 8 | 4 | 1 | Yes | 2 |
| 9 | 5 | 2 | Yes | 2 |
| 10 | 3 | 1 | Yes | 2.5 |

No evaluation on healing of the lesions and extent of inflammation of the oral mucosa was observed in this trial. In all of the cases, the patients indicated a remarkable improvement in oral function after treatment, allowing the ability to speak, eat, and perform daily activities such as teeth brushing and flossing.

Lollipop Example

Patients were treated with a composition formed with an herbal composition having ingredients as shown in the table below. The table also provides suitable ranges for each ingredient as may be used in an herbal composition in a gum formulation. The w/w percentages listed in the below table are based on the weight of the lollipop, as described below.

Composition (% of weight-weight) of individual herbal ingredients for lollipop

| Ingredients | % (w/w) | Ranges % (w/w) |
| --- | --- | --- |
| Annatto | 2.2% | 0.05-30% |
| Cayenne | 0.62% | 0.01-20% |
| Cinnamon | 0.95% | 0.25-40% |
| Cloves | 1.2% | 0.01-30% |
| Ginger | 1.1% | 0.01-40% |
| Turmeric | 1.7% | 0.25-60% |

The herbal composition as described above can be formulated into a lollipop composition as shown in the table below. In should be understood that other candy formulations, as known to one skilled in the art, may be used in the present invention.

Ingredients for lollipop (242 g total, 5 g each lollipop)

| Ingredient | Amount |
| --- | --- |
| Granulated Sugar | 150 g |
| Corn Syrup | 58 g |
| Water | 15 ml |
| Herbal Composition | 19 g |

The composition was delivered via a candy lollipop weighing 5 g each. Patients were assessed every 15 minutes over a 2-3 hour time period. Prior to treatment, the following steps were undertaken: 1) visual diagnosis focusing on the minor ulcer with a well-demarcated ulcer on the non-keratinized oral mucosa, and 2) patients were asked to complete a pre-treatment VAS.

Patients were directed to suck on the lollipop until they noticed a reduction in pain and, if desired, to place the lollipop near the area of oral inflammation. Similar to the gum, saliva production and release of the composition provided uniform distribution on the whole surface of the oral mucosa. The average time of contact was 30 minutes. Patients were not refrained from eating or drinking immediately after sucking the lollipop. Patients had the ability to remove the lollipop if they were uncomfortable or felt that pain relief was adequate. Pain relief was noticeable within 10 minutes of sucking on the lollipop and patients perceived pain was reduced by 50-80%. The effect lasted up to two hours, and patients indicated that the composition tasted good and was well tolerated. All patients reported comparable pain relief on subsequent uses of the lollipop until resolution of canker sore. The table below provides the pre- and post-treatment VAS scores.

Pre and Post Treatment VAS Scores (10 cm) using lollipop

| Patient | Pain before candy | Pain after candy | Pain Relief | Duration of relief (hrs) |
| --- | --- | --- | --- | --- |
| 1 | 6 | 2 | Yes | 1 |
| 2 | 6 | 3 | Yes | 1.5 |
| 3 | 5 | 2 | Yes | 1.5 |
| 4 | 4 | 1 | Yes | 1.5 |
| 5 | 5 | 2 | Yes | 1 |
| 6 | 5 | 1 | Yes | 1 |
| 7 | 6 | 2 | Yes | 1 |
| 8 | 6 | 2 | Yes | 1 |
| 9 | 7 | 3 | Yes | 1.5 |
| 10 | 4 | 1 | Yes | 1 |

No evaluation on healing of the lesions and extent of inflammation of the oral mucosa was observed in this trial. In all of the cases, the patients indicated a remarkable improvement in oral function after treatment, allowing the ability to speak, eat, and perform daily activities such as teeth brushing and flossing.

As used herein, the term "inactive ingredients" refer to those ingredients in a formulation in addition to the designated active ingredients. Such inactive ingredients can include sugar, corn syrup, gums, water, and the like. Such inactive ingredients can include those ingredients used to formulate the herbal composition into a gum, candy, or the like. Active ingredients can include those described above in the herbal composition according to aspects of the present invention.

As used herein, "treatment" includes preventative (e.g., prophylactic) and palliative treatment and "treating" as used herein refers to the act of providing preventative and/or palliative treatment.

The term "therapeutically effective amount" means an amount of a formulation or compound or a combination of a formulation or compound with additional compounds that ameliorates one or more symptom or prevents or delays the onset of one of more symptom of a disease or condition.

As used herein, "patient" means mammals, particularly humans.

As used herein, a patient "in need" of a composition includes a patient that has an active condition for which the composition can treat, or a patient that seeks prevention of such condition.

All the features disclosed in this specification, including any accompanying abstract and drawings, may be replaced by alternative features serving the same, equivalent or similar purpose, unless expressly stated otherwise. Thus, unless expressly stated otherwise, each feature disclosed is one example only of a generic series of equivalent or similar features.

Claim elements and steps herein may have been numbered and/or lettered solely as an aid in readability and understanding. Any such numbering and lettering in itself is not intended to and should not be taken to indicate the ordering of elements and/or steps in the claims.

Many alterations and modifications may be made by those having ordinary skill in the art without departing from the spirit and scope of the invention. Therefore, it must be understood that the illustrated embodiments have been set forth only for the purposes of examples and that they should not be taken as limiting the invention as defined by the following claims. For example, notwithstanding the fact that the elements of a claim are set forth below in a certain combination, it must be expressly understood that the invention includes other combinations of fewer, more or different ones of the disclosed elements.

The words used in this specification to describe the invention and its various embodiments are to be understood not only in the sense of their commonly defined meanings, but to include by special definition in this specification the generic structure, material or acts of which they represent a single species.

The definitions of the words or elements of the following claims are, therefore, defined in this specification to not only include the combination of elements which are literally set forth. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptually equivalent, what can be obviously substituted and also what incorporates the essential idea of the invention.

What is claimed is:

1. A formulation comprising active ingredients including:
   from about 2 to about 70 weight percent annatto;
   from about 0.05 to about 40 weight percent of a capsaicinoid; and
   from about 0.1 to about 60 weight percent ginger.

2. The formulation of claim 1, further comprising from about 0.05 to about 50 weight percent cloves.

3. The formulation of claim 1, further comprising from about 5 to about 30 weight percent cinnamon.

4. A formulation of claim 1, further comprising from about 1 to about 70 weight percent turmeric.

5. The formulation of claim 1, further comprising:
   from about 0.05 to about 50 weight percent cloves;
   from about 5 to about 30 weight percent cinnamon; and
   from about 1 to about 70 weight percent turmeric.

6. The formulation of claim 5, wherein:
   the annatto is present from about 20 to about 36 weight percent;
   the capsaicinoid is cayenne which is present from about 5.6 to about 10.4 weight percent;
   the cinnamon is present from about 8.4 to about 16 weight percent;
   the cloves are present from about 11 to about 21 weight percent;
   the ginger is present from about 10 to about 18 weight percent; and
   the turmeric is present from about 15 to about 29 weight percent.

7. The formulation of claim 5, wherein:
   the annatto is present at 28 weight percent;
   the capsaicinoid is cayenne which is present at 8 weight percent;
   the cinnamon is present at 12 weight percent;
   the cloves are present at 16 weight percent;
   the ginger is present at 14 weight percent; and
   the turmeric is present at 22 weight percent.

8. The formulation of claim 1, further comprising inactive ingredients operable to form a gum.

9. The formulation of claim 8, wherein the inactive ingredients include confectioner's sugar, corn syrup and gum pellets.

10. The formulation of claim 8, wherein the active ingredients are present at about 5 to about 20 weight percent of the gum.

11. The formulation of claim 8, wherein the active ingredients are present at about 10 to about 15 weight percent of the gum.

12. The formulation of claim 8, wherein the active ingredients are present at about 12 weight percent of the gum.

13. The formulation of claim 1, further comprising inactive ingredients operable to form a hard candy.

14. The formulation of claim 13, wherein the inactive ingredients include granulated sugar, corn syrup and water.

15. The formulation of claim 13, wherein the active ingredients are present at about 3 to about 20 weight percent of the hard candy.

16. The formulation of claim 13, wherein the active ingredients are present at about 6 to about 10 weight percent of the hard candy.

17. The formulation of claim 13, wherein the active ingredients are present at about 7.8 weight percent of the hard candy.

18. The formulation of claim 13, wherein the hard candy is a lollipop.

19. The formulation of claim 1, wherein the capsaicinoid is obtained from cayenne.

20. The formulation of claim 1, wherein the capsaicinoid is selected from at least one of capsaicin, dihydrocapsaicin, norhydrocapsaicin, homocapsaicin, homodihydrocapsaicin I, norhydrocapsaicin, homodihydrocapsaicin, nordihydrocapsaicin, civamide, nonivamide, NE-19550, NE-21610, NE-28345, or derivatives or analogs thereof.

21. A formulation comprising active ingredients including:
   from about 0.05 to about 28 weight percent annatto;
   from about 0.05 to about 8 weight percent of a capsaicinoid;
   from about 1 to about 22 weight percent turmeric; and
   from about 1.9 to about 21 weight percent cloves.

22. The formulation of claim 21, further comprising from about 0.1 to about 60 weight percent ginger.

23. The formulation of claim 21, further comprising from about 5 to about 30 weight percent cinnamon.

24. The formulation of claim 21, wherein the capsaicinoid is one or more of cayenne, capsaicin, dihydrocapsaicin, norhydrocapsaicin, homocapsaicin, homodihydrocapsaicin I, norhydrocapsaicin, homodihydrocapsaicin, nordihydrocapsaicin, civamide, nonivamide, NE-19550, NE-21610, NE-28345 or analogs and derivatives thereof.

25. The formulation of claim 21, wherein the formulation is one of a gum or a lollipop.

26. The formulation of claim 25, wherein the active ingredients are present at about 3 to about 20 weight percent of the composition.

27. The formulation of claim 21, wherein the capsaicinoid is formed from cayenne.

* * * * *